US010503157B2

(12) United States Patent
Endrerud et al.

(10) Patent No.: US 10,503,157 B2
(45) Date of Patent: Dec. 10, 2019

(54) REMOTE NON-DESTRUCTIVE TESTING

(71) Applicant: DolphiTech AS, Gjøvik (NO)

(72) Inventors: Jan Olav Endrerud, Gjøvik (NO); Eskil Skoglund, Gjøvik (NO)

(73) Assignee: DolphiTech AS, Gjøvik (NO)

( * ) Notice: Subject to any disclaimer, the term of this patent is extended or adjusted under 35 U.S.C. 154(b) by 508 days.

(21) Appl. No.: 14/855,931

(22) Filed: Sep. 16, 2015

(65) Prior Publication Data

US 2016/0077522 A1 Mar. 17, 2016

(30) Foreign Application Priority Data

Sep. 17, 2014 (GB) .................................. 1416443.8
Jun. 1, 2015 (GB) .................................. 1509435.2

(51) Int. Cl.
*G05B 23/00* (2006.01)
*H04L 29/08* (2006.01)
*G06F 11/00* (2006.01)
*G01N 29/44* (2006.01)
*G01N 29/04* (2006.01)
*G01N 29/06* (2006.01)

(52) U.S. Cl.
CPC .......... *G05B 23/00* (2013.01); *G01N 29/043* (2013.01); *G01N 29/0645* (2013.01); *G01N 29/449* (2013.01); *G06F 11/00* (2013.01); *H04L 67/12* (2013.01); *G01N 2291/0258* (2013.01); *G01N 2291/044* (2013.01)

(58) Field of Classification Search
CPC ... G05B 23/00; G01N 29/043; G01N 29/0645

USPC .......................................................... 702/188
See application file for complete search history.

(56) References Cited

U.S. PATENT DOCUMENTS

| 3,778,756 A | 12/1973 | Houston |
| 3,895,525 A | 7/1975 | Eichelberger et al. |
| 4,441,369 A | 4/1984 | Lessard et al. |

(Continued)

FOREIGN PATENT DOCUMENTS

| CN | 102680583 | 9/2012 |
| DE | 20213105252 | 4/2014 |

(Continued)

OTHER PUBLICATIONS

European Search Report issued in EP application No. 15184642.5 dated Mar. 24, 2016, 8 pages.

(Continued)

*Primary Examiner* — Anthan Tran
(74) *Attorney, Agent, or Firm* — Fish & Richardson P.C.

(57) ABSTRACT

An inspection apparatus for enabling a remotely-located expert to monitor an inspection by a non-expert, the apparatus comprising an inspection device capable of being operated by the non-expert, which is configured to generate inspection data indicative of a condition of a test object, and a communication unit configured to: divide the inspection data into first and second data; transfer the first data for being presented to the remotely-located expert at a first time, to facilitate substantially real-time monitoring of the inspection by the expert; and transfer the second data for being presented to the remotely-located expert at a second time, which is later than the first time, to facilitate non-real time monitoring of the inspection by the expert.

18 Claims, 10 Drawing Sheets

(56) References Cited

U.S. PATENT DOCUMENTS

| | | | |
|---|---|---|---|
| 5,383,366 | A | 1/1995 | Wallingford et al. |
| 5,773,811 | A | 6/1998 | Schramm, Jr. et al. |
| 6,748,259 | B1 | 6/2004 | Benaron |
| 7,478,569 | B2 | 1/2009 | Bossi et al. |
| 7,617,730 | B2 | 11/2009 | Georgeson |
| 7,675,045 | B1 | 3/2010 | Werner |
| 8,255,170 | B2 | 8/2012 | Kollgaard et al. |
| 8,453,928 | B2 | 6/2013 | Melandsø et al. |
| 2001/0037366 | A1 | 11/2001 | Webb et al. |
| 2002/0062083 | A1 | 5/2002 | Ohara et al. |
| 2003/0145655 | A1 | 8/2003 | Lorraine et al. |
| 2005/0279171 | A1 | 12/2005 | Kollgaard |
| 2006/0219013 | A1 | 10/2006 | Baba et al. |
| 2007/0084290 | A1 | 4/2007 | Fetzer et al. |
| 2008/0000299 | A1 | 1/2008 | Georgeson |
| 2008/0208061 | A1 | 8/2008 | Halmann |
| 2008/0301152 | A1 | 12/2008 | Kollgaard et al. |
| 2009/0082673 | A1 | 3/2009 | Lu et al. |
| 2010/0274139 | A1 | 10/2010 | Fukukita et al. |
| 2011/0040187 | A1 | 2/2011 | Matsumura |
| 2012/0192651 | A1 | 8/2012 | Lee et al. |
| 2013/0030727 | A1 | 1/2013 | Zalameda et al. |
| 2013/0163430 | A1* | 6/2013 | Gell ............... H04N 21/23439 370/235 |
| 2014/0139658 | A1* | 5/2014 | Dhanvantri .......... G01N 21/954 348/85 |
| 2015/0186896 | A1* | 7/2015 | Vass .................. G06Q 30/018 705/317 |

FOREIGN PATENT DOCUMENTS

| | | |
|---|---|---|
| EP | 1621135 | 11/2006 |
| EP | 2249152 | 11/2010 |
| GB | 2109555 | 6/1983 |
| GB | 2286678 | 8/1995 |
| GB | 2432671 | 5/2007 |
| JP | 60-102553 | 6/1985 |
| JP | 60-102554 | 6/1985 |
| JP | 08-075714 | 3/1996 |
| JP | 2010060520 A | 3/2010 |
| WO | WO2008/137030 | 11/2008 |
| WO | WO2011/089537 | 7/2011 |
| WO | WO2013/161834 | 10/2013 |

OTHER PUBLICATIONS

[Online] 1 Introduction to DolphiCam, Published on Aug. 7, 2013 by DolphiTech, to be accessed online at <https://www.youtube.com/watch?v=uPZnT78L_PE> Feb. 16, 2016.
[Online] 2 Unboxing, Published on Aug. 7, 2013 by DolphiTech, to be accessed online at <https://www.youtube.com/watch?v=wcvStX941B0> Feb. 16, 2016.
[Online] 3 The Camera, Published on Aug. 7, 2013, by DolphiTech, to be accessed online at <https://www.youtube.com/watch?v=-G9aJkBdegM> Feb. 16, 2016.
[Online] 4 Getting Started, Published on Aug. 7, 2013 by DolphiTech, to be accessed online at < https://www.youtube.com/watch?v=x_hhrKvGPgk> Feb. 16, 2016.
[Online] 5 Calibrating and Scanning, Published on Aug. 7, 2013 by DolphiTech, to be accessed online at <https://www.youtube.com/watch?v=jNNrN5C-Gz4> Feb. 16, 2016.
[Online] 6 Scanning Boreholes, Published on Aug. 7, 2013 by DolphiTech, to be accessed online at < https://www.youtube.com/watch?v=FUd0SGe9UDg> Feb. 16, 2016.
[Online] 7 Scanning Impact Damages, Published on Aug. 7, 2013 by DolphiTech, to be accessed online at < https://www.youtube.com/watch?v=iI2bDgwL4Yg> Feb. 16, 2016.
[Online] 8 3D Visualization, Published on Aug. 7, 2013 by DolphiTech, to be accessed online at < https://www.youtube.com/watch?v=TGcKxyAq_p0> Feb. 16, 2016.
[Online] 9 Caring for the Camera, Published on Aug. 7, 2013 by DolphiTech, to be accessed online at < https://www.youtube.com/watch?v=LdgmJX9SS0E> Feb. 16, 2016.
UK Intellectual Property Office, Search Report, Application No. GB1413618.8, dated Jan. 27, 2015, 2 pages.
UK Intellectual Property Office, Search Report, Application No. GB1413616.2, dated Jan. 28, 2015, 2 pages.
UK Intellectual Property Office, Search Report, Application No. GB1315090.9, dated Jan. 30, 2015, 2 pages.
Cincotti et al.: "Efficient transmit beamforming in pulse-echo ultrasonic imaging", IEEE Transactions on Ultrasonics, Ferroelectrics and Frequency Control, IEEE, US, vol. 46, No. 6, Nov. 1, 1999, pp. 1450-1458, XP011438016.
Data Presentation. (Jun. 25, 2003). Retrieved Jan. 19, 2016, from http://www.nde-ed.org/EducationResources/CommunityCollege/Ultrasonics/EquipmentTrans/DataPres.htm.
Endrerud, Jan Olav; Skoglund, Eskil: "DolphiCam User Manual", Jun. 27, 2013, XP055179749, Raufoss, Noway, http://www.dolphitech.com/wp-content/uploads/2014/12/DolphiCam-User-Manual-1.1-27.06.2013.pdf.
European Extended Search Report issued in EP application No. 14185307.7 dated Apr. 20, 2015, 7 pages.
Gustafsson, M. G., et al., "Split Spectrum Algorithms Rely on Instantaneous Phase Information—A Geometrical Approach," IEEE Transactions on Ultrasonics, Ferroelectrics, and Frequency Control, vol. 40, No. 6, Nov. 1993, pp. 659-665.
Niblack, Wayne, "Digital Image Processing," 1986 Prentice-Hall International, 217 pages.
Olympus NDT. EPOCH 1000 Series User's Manual. 910-269-EN—Revision B Jun. 2011.
Persson et al.: "Electric excitation of ultrasound transducers for short pulse generation", Ultrasound in Medicine and Bioligy, New York, NY, US, vol. 7, No. 3, Jan. 1, 1981, pp. 285-289, 291, XP026374039.
Rubbers, Philippe, et al., "An Overview of Split Spectrum Processing," NDT.net Aug. 2003, vol. 8, No. 8, http://www.ndt.net/article/v08n08/rubbers.htm, 10 pages.
Stoica, Petre, et al., "Transmit Codes and Receive Filters for Radar," IEEE Signal Processing Magazine, Nov. 2008, pp. 94-109.
Tian, Qi, et al., "Multiple Target Detection Using Split Spectrum Processing and Group Delay Moving Entropy," IEEE Transactions on Ultrasonics, Ferroelectrics, and Frequency Control, vol. 42, No. 6, Nov. 1995, pp. 1076-1086.
Tomasi, C., et al., "Bilateral Filtering for Gray and Color Images," Proceedings of the 1998 IEEE International Conference on Computer Vision, Bombay, India, 8 pages.
Ultrasound and Ultrasonic Testing. (May 19, 2003). Retrieved Jan. 19, 2016, from http://www.nde-ed.org/EducationResources/HighSchool/Sound/ubrasol.ncl.htm.
European examination report for corresponding 15184642.5, dated Jan. 3, 2019.

* cited by examiner

REMOTE NON-DESTRUCTIVE TESTING

CROSS-REFERENCE TO RELATED APPLICATION

This application claims priority to UK Patent Application No. 1509435.2 entitled Remote Non-Destructive Testing, which was filed on 1 Jun. 2015 which claims priority to UK Patent Application No. 1416443.8 entitled Remote Non-Destructive Testing, which was filed on 17 Sep. 2014, both of which are herein incorporated in their entirety by reference.

BACKGROUND

This invention relates to an inspection apparatus and method, and in particular to an inspection apparatus and method for non-destructively inspecting the sub-surface structure of a test object.

The term "non-destructive testing" encompasses a number of techniques that can be used to evaluate the properties of a material, component or system without causing damage. These techniques are particularly used in the automotive and aerospace industries to assess sub-surface damage or material flaws. It is vital that this work is carried out to a high standard in the aerospace industry particularly, since damage that is not visible on the external surface of the aircraft may nonetheless compromise its structural integrity in the air. For this reason aerospace authorities apply stringent conditions to those who are authorised to inspect aircraft and pronounce them fit to fly. An aircraft often needs to be inspected at a location where there are not any individuals that are sufficiently qualified to undertake that inspection, however.

SUMMARY

According to a first aspect, there is provided an inspection apparatus for enabling a remotely-located expert to monitor an inspection by a non-expert, the apparatus comprising an inspection device capable of being operated by the non-expert, which is configured to generate inspection data indicative of a condition of a test object and a communication unit configured to: divide the inspection data into first and second data; transfer the first data for being presented to the remotely-located expert at a first time, to facilitate substantially real-time monitoring of the inspection by the expert; and transfer the second data for being presented to the remotely-located expert at a second time, which is later than the first time, to facilitate non-real time monitoring of the inspection by the expert.

Implementations may include one or more of the following features. An inspection device capable of generating data indicative of an interior structure of the object, without damaging said object. A communication unit configured to divide the inspection data such that the first data comprises fewer bytes that the second data. A communication unit configured to divide the inspection data such that the first data has been subject to more processing than the second data. A communication unit configured to divide the inspection data such that the second data is raw data. A communication unit configured to divide the inspection data such that the second data comprises data indicative of a more detailed representation of the object's condition than the first data, whereby the second data facilitates a more in-depth analysis of the inspection by the remotely located expert than the first data. A communication unit configured to transfer the first data before the second data. A communication unit configured to transfer the first data at a higher data rate than the second data. A communication unit configured to transfer the first data over a higher capacity communication link than the second data. A buffer configured to store the second data before the communication unit transfers it. A communication unit configured to: receive a request from the remotely-located expert for the second data; retrieve the requested data from the buffer; and transfer the requested data to the remotely-located expert.

According to a second aspect, there is provided a method for enabling a remotely-located expert to monitor an inspection by a non-expert, the method comprising generating inspection data indicative of a condition of a test object, dividing the inspection data into first and second data, transferring the first data for being presented to the remotely-located expert at a first time, to facilitate substantially real-time monitoring of the inspection by the expert and transferring the second data for being presented to the remotely-located expert at a second time, which is later than the first time, to facilitate non-real time monitoring of the inspection by the expert.

According to a third aspect, there is provided an inspection apparatus for enabling a remotely-located expert to monitor an inspection by a non-expert, the apparatus comprising a communication unit configured to receive inspection data from an inspection device operated by the non-expert, a user interface configured to present the inspection data to the expert and a division unit configured to recognise, in the inspection data, first data for being presented to the expert at a first time, to facilitate substantially real-time monitoring of the inspection by the expert, and second data for being presented to the expert at a second time, which is later than the first time, to facilitate non-real time monitoring of the inspection by the expert.

Implementations may include one or more of the following features. A user interface configured to, when the division unit recognises first data, present that first data to the expert directly. A buffer configured to store the second data until it is requested by the expert. A user interface configured to only present the second data when it is requested by the expert. A processing unit configured to manipulate the second data responsive to a control input from the expert.

According to a fourth aspect, there is provided a method for enabling a remotely-located expert to monitor an inspection by a non-expert, the apparatus comprising receiving inspection data from an inspection device operated by the non-expert, presenting the inspection data to the expert and recognising, in the inspection data, first data for being presented to the expert at a first time, to facilitate substantially real-time monitoring of the inspection by the expert, and second data for being presented to the expert at a second time, which is later than the first time, to facilitate non-real time monitoring of the inspection by the expert.

According to a fifth aspect, there is provided an inspection apparatus, comprising an inspection device configured to generate inspection data representative of a material structure below a surface of a test object, an image generator configured to generate a visual representation of the material structure from the inspection data, and a projection device configured to project the visual representation of the material structure onto either the test object or a visual representation thereof.

Implementations may include one or more of the following features. A projection device configured to project the visual representation of the material structure onto a surface of the test object or onto a visual representation thereof. A projection device configured to project the visual representation of the material structure onto a part of the test object's surface that corresponds to the part below which the visual representation represents the material structure. A projection device configured to project a visual representation of a structure below an outer surface of the test object onto that outer surface or a visual representation thereof. A projection device configured to project a visual representation of a previous repair and/or damage to the test object onto the surface of the test object or a visual representation thereof. A projection device configured to combine said projection of the visual representation of the structure below the test object's outer surface or said projection of the visual representation of a previous repair and/or damage with the projection of the visual projection of the material structure. A projection device being configured to project the visual representation of the material structure onto a 3D CAD model.

According to a sixth aspect, there is provided a method comprising generating inspection data representative of a material structure below a surface of a test object, generating a visual representation of the material structure from the inspection data, and projecting the visual representation of the material structure onto either the test object or a visual representation thereof.

According to a seventh aspect, there is provided an inspection apparatus for enabling a remotely-located expert to control an inspection by a non-expert, the apparatus comprising an inspection device capable of being operated by a non-expert, which is configured to generate inspection data indicative of a condition of a test object and a visual guide configured to provide, to the non-expert, a visual indication of a location on the test object to be inspected in dependence on a control input from the remotely-located expert.

Implementations may include one or more of the following features. A visual guide being configured to provide a visual indication of a direction in which the non-expert should move the inspection device. A visual guide comprising a projection device configured to project the visual indication onto the test object. A visual guide comprising a laser. An inspection device that comprises the visual guide.

According to an eighth aspect, there is provided a method for enabling a remotely-located expert to control an inspection by a non-expert, the method comprising generating inspection data indicative of a condition of a test object and providing, to the non-expert, a visual indication of a location on the test object to be inspected in dependence on a control input from the remotely-located expert.

According to a ninth aspect, there is provided a directory for connecting a non-expert inspector with a remotely-located expert, the directory comprising a communication unit configured to receive a request from an inspection apparatus for an expert, a memory configured to store contact information for a plurality of experts and a selection unit configured to extract, from the request, one or more criteria for the expert and select, in dependence on those criteria, a remotely-located expert.

Implementations may include one or more of the following features. A selection unit configured to extract criteria including one or more of: a location of the inspection apparatus, a type of test object being inspected by the inspection apparatus, an owner of the test object being inspected by the inspection apparatus and a legal requirement governing the inspection of the test object. A communication unit configured to connect the inspection apparatus to the selected expert. A communication unit configured to return contact information for the selected expert to the inspection apparatus.

According to a tenth aspect, there is provided a method connecting a non-expert inspector with a remotely-located expert, the method comprising receiving a request from an inspection apparatus for an expert, storing contact information for a plurality of experts and extracting, from the request, one or more criteria for the expert and select, in dependence on those criteria, a remotely-located expert.

According to an eleventh aspect, there is provided an inspection apparatus for enabling a remotely-located expert to monitor an inspection by a non-expert, the inspection apparatus comprising a user interface configured to receive an instruction from the non-expert for a monitored inspection and a communication unit configured to automatically contact a directory responsive to the instruction to request a remotely-located expert.

Implementations may include one or more of the following features. A communication unit configured to request that the directory automatically connect the inspection apparatus to a remotely-located expert. A communication unit configured to receive contact information from the remotely-located expert and use that contact information to automatically establish a connection between the inspection apparatus and the remotely-located expert.

According to a twelfth aspect, there is provided an inspection apparatus comprising a projection device configured to project, onto the surface of a test object or a visual representation thereof, an image representing information that is relevant to the integrity of the test object.

Implementations may include one or more of the following features. A projection device configured to project an image representative of a material structure of the test object. A projection device being configured to project an image representative of a structure below the outer surface of the test object. A projection device being configured to project an image representative of previous damage and/or repair to the test object.

According to a twelfth aspect, there is provided a method for inspecting a test object comprising projecting, onto the surface of a test object or a visual representation thereof, an image representing information that is relevant to the integrity of the test object.

According to a thirteenth aspect, there is provided an inspection apparatus comprising a position determination unit configured to determine a position of an inspection device relative to a test object and a configuration unit configured to select configuration data in dependence on that position, said configuration data being capable of configuring the inspection device to generate inspection data indicative of a condition of the test object, and provide that configuration data to the inspection device.

The position determination unit may be configured to identify a part of the test object that is associated with the position of the inspection device relative to the test object.

The configuration unit may be configured to select the configuration data in dependence on the identified part.

The inspection apparatus may comprise a database that is configured to store configuration data in association with one or more parts of the test object.

The inspection apparatus may comprise a user interface configured to, if the position determination unit identifies more than one part of the test object that is associated with the position of the inspection device relative to the test object: indicate to the user that more than one part has been identified, receive an input from the user indicative of the user having selected one of the identified parts and inform the configuration unit of the selected one of the identified parts.

The configuration unit may be configured to provide the inspection device with configuration data associated with the selected one of the identified parts.

According to a fourteenth aspect, there is provided a method comprising determining a position of an inspection device relative to a test object, selecting configuration data in dependence on that position, said configuration data being capable of configuring the inspection device to generate inspection data indicative of a condition of the test object and providing that configuration data to the inspection device.

The present invention will now be described by way of example with reference to the accompanying drawings. In the drawings:

DETAILED DESCRIPTION

Figure 1:
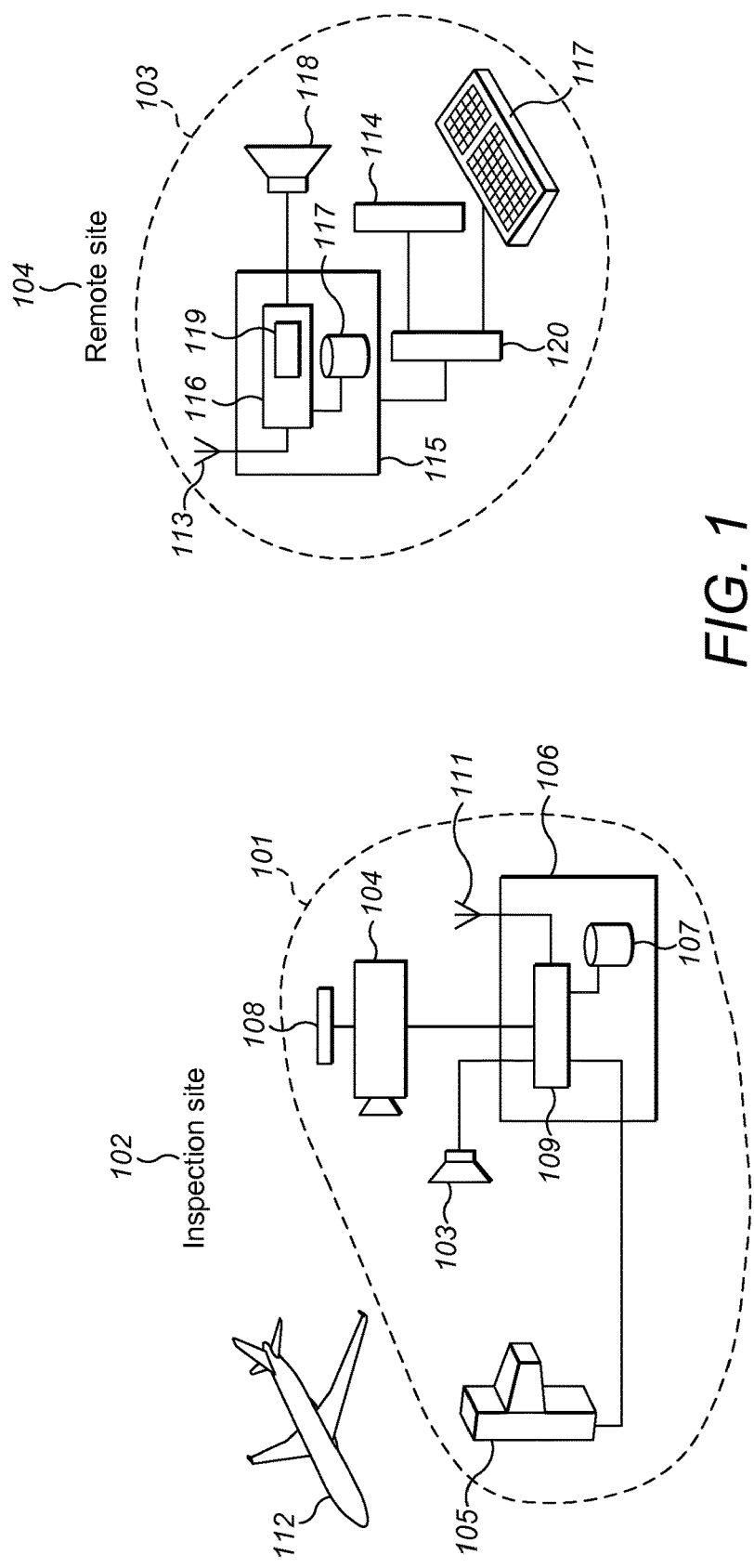
FIG. 1 shows an inspection apparatus at an inspection site and at a remote site.

An example of an apparatus for inspecting a test object remotely is shown in FIG. 1. The apparatus is formed of two parts: a first part 101 located at an inspection site 102 and a second part 103 located at a remote site 104. The first part of the inspection apparatus comprises an inspection device 105. The inspection device is suitably capable of gathering information about a range of different materials, including metals, plastics, composites, carbon fibre etc.

The inspection device is preferably capable of being operated by a non-expert. In this scenario a "non-expert" may be someone who is not authorised to perform inspection procedures on a particular test object without supervision. For example, the test object in this example is aeroplane 112, and the non-expert may be a local mechanic who has not been certified by the aeroplane's owners as being authorised to undertake repair decisions with respect to the aeroplane. The expert will typically be someone who does have the appropriate authorisation. The expert is thus able to make decisions on the basis of inspection data. Those decisions could include whether an aeroplane is fit to fly, for example, or whether it needs to be repaired, in which case the expert may decide what type of repair is appropriate. The expert will often not be in the same place as the aeroplane. The expert can thus be considered to be remotely located: the expert is located at a sufficient distance from the test object that he cannot undertake the physical inspection himself and is reliant on the non-expert to gather the necessary inspection data. It is thus likely that the inspection data will have to be transferred from the inspection site to the remote expert's location via a communication link. This link may be wired or wireless.

When operated, the inspection device 105 gathers data that indicates the condition of the test object. This data may be representative of a material structure of the test object beneath its surface. Preferably the inspection device is capable of non-destructive testing, i.e. evaluating the material under test without causing damage. Suitable non-destructive testing techniques include magnetic particle, liquid penetrant, eddy current testing and low coherence inferometry. In a preferred embodiment the inspective device uses ultrasound to gather information about the test object. For example, the inspection device may be configured to fire a series of ultrasound pulses at the test object and receive reflections of those pulses back from the test object. The reflected pulses can be used to make inferences about the sub-surface structure of the test object and particularly about issues such as voids, delamination and impact damage, some of which may not be visible on the surface. In a preferred embodiment, inspection data generated by the inspection device is used to generate images of the test object. These images may include one or more of A-scans, B-scans, C-scans and 3D representations.

Data gathered by the inspection device will usually have to be processed before it can be used to form other images or other useful output. This processing might be performed at the inspection site or at the remote site. It might be performed in the inspection device itself or in an associated computing device (not shown). The requiring processing may include one or more of filtering, time averaging, thresholding, signal envelope estimation, normalisation, image generation etc. For the purposes of this disclosure it does not matter exactly what processing is performed on the data gathered by the inspection device nor where that data is processed. It should be understood that the term "inspection data" is used herein to refer generally to any data that originates with the inspection device, irrespective of what form that data takes or whether it has been processed after being captured by the inspection device.

The apparatus at the inspection site may be provided with a user interface, such as a display, that the non-expert can use to view images generated by the inspection device. This user interface is not shown in FIG. 1. A user interface is shown as being part of the inspection apparatus 104 at the remote site. In this example the user interface takes the form of a keyboard 117 and a display 114, both of which might form part of a PC or other computing device. The user interface is preferably configured to present inspection data gathered by the inspection device to the remote expert. In one example this presentation takes the form of an image or video shown on a display but any other suitable form of presentation might be used.

In the arrangement of FIG. 1 the inspection apparatus at the inspection and remote sites are configured to exchange data via a wireless link. In other examples the connection between the two sites will be via a wire. Equally the link could be a combination of wired and wireless, e.g. the inspection apparatus might communicate wirelessly with a router, which routes data to the remote site over the internet. Both apparatus include a respective communicator 106, 115. In the apparatus at the inspection site the communicator 106 comprises a communication unit 109 that is connected to receive inspection data from inspection device 105. The communication unit is also connected to an antenna 111. The communication unit may be configured to communicate data according to any suitable protocol. In this example the communication unit is configured for wireless communication, so an appropriate protocol might be WiFi, Bluetooth, LTE, GSM etc., possibly utilizing Web Real Time Communications (Web RTC) protocol or similar. WebRTC is described in more detail below. The communicator 115 at the inspection site is similarly arranged, comprising antenna 113 and communication unit 116.

Figure 2:
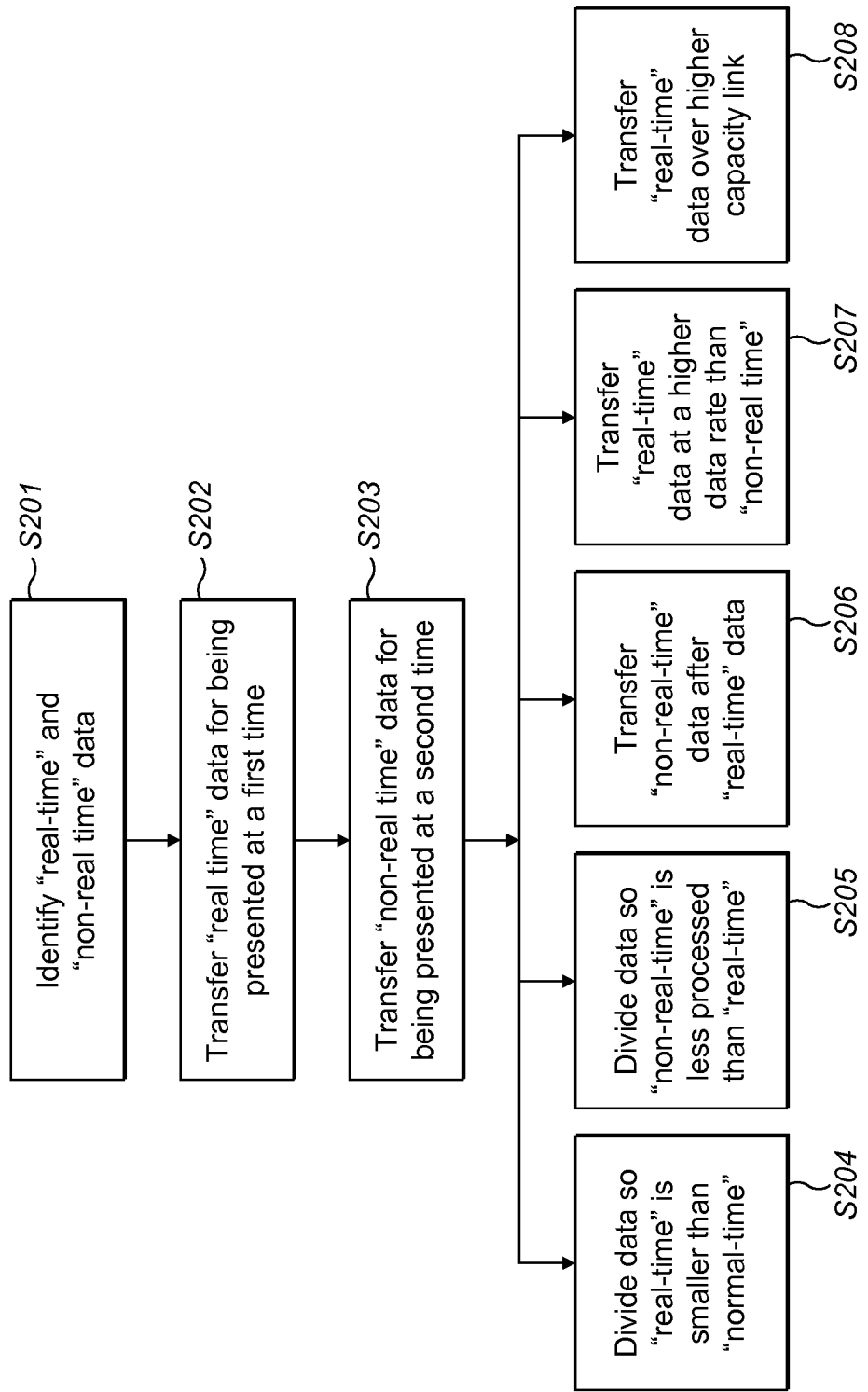
FIG. 2 shows an example of a method of operating an inspection apparatus.

In a preferred implementation the expert is able to interact with the non-expert. It is preferable in this scenario for the expert to be able to monitor the inspection in real-time but practical limitations such as cost and bandwidth constraints may make this unrealistic. To address this, communication unit 109 may be configured to divide the data that it receives from the inspection device into "real-time" data and "non-real time" data. This process is shown in FIG. 2.

First the communication unit identifies which data should be presented to the remote expert substantially in real-time and which can be presented in non-real time (step S201). The "real-time" data is transferred for being presented to the remotely-located apparatus at a first time (step S202). The aim of this transfer is to facilitate substantially real-time monitoring of the inspection by the expert. For practical reasons the "first time" will not be exactly the same as the time at which the data is captured by the inspection device because it inevitably takes some time to process that data into a form that can be presented to the remote expert and to transfer data between the two sites. The presentation of the data to the remote expert therefore preferably occurs in "substantially real-time", so that the data is presented quickly enough after the capture of the inspection data for the remote expert to be able to issue meaningful instructions/guidance to the expert who is handling the inspection device. The remaining data is "non-real time" data. The communication unit transfers it for being presented to the remotely-located expert at a second time (step S203). The second time is preferably later than the first time, i.e. the non-real time data will be available for monitoring by the remote expert at a later time than the "real-time". It is envisaged that the non-real time data will be data that the expert can use to gain a more detailed understanding of the condition of the test object. For example, the non-real time data may represent a more complex type of image than the non-real time data, such as a 3D representation, or a time-data series, compared with an A-scan image.

There are a number of different options for the inspection apparatus to manage the transfer of inspection data to the remote site. Some of these options are shown in FIG. 2. One option is for the communication unit just to divide the data up so that the real-time data has fewer bytes than the non-real time data, enabling it to be transferred more quickly across a given communication link (step S204). The real-time data may have been subject to extra processing compared with the non-real-time data (step S205). For example, the non-real time data may be "raw" data, subject to only a minimal amount of processing after its capture by the inspection device. The expert may be able to manipulate this data at the remote location, so the raw data can enable the expert to undertake a more detailed analysis of the test object than is possible from the non-real time data alone. A processing unit 120 may be provided in the remote apparatus for this purpose. Other options involve the communication unit prioritising the transfer of real-time data. For example, another option is for the communication unit to transfer the non-real time data after the real-time data (step S206). For example, the non-real time data may only be transferred when the inspection device ceases to capture new data. The inspection apparatus may comprise a buffer configured to store non-real time data before it is transferred (this buffer is represented by memory 107 in FIG. 1). The communication unit might also transfer the real-time data at a higher data rate than the non-real time data (step S207). This might free up some capacity over the communication link for other data (e.g. real-time data). All of the preceding options would enable the real-time and non-real time data to be transferred over the same communication link, but the two types of data could equally be transferred across different communication links. For example, the communication unit may transfer the real-time data over a higher capacity communication link that the non-real time data (step S208). It should be understood that the communication unit might readily combine two or more of the methods shown at S204 to S208 in FIG. 2, as well as implementing them individually.

Figure 3:
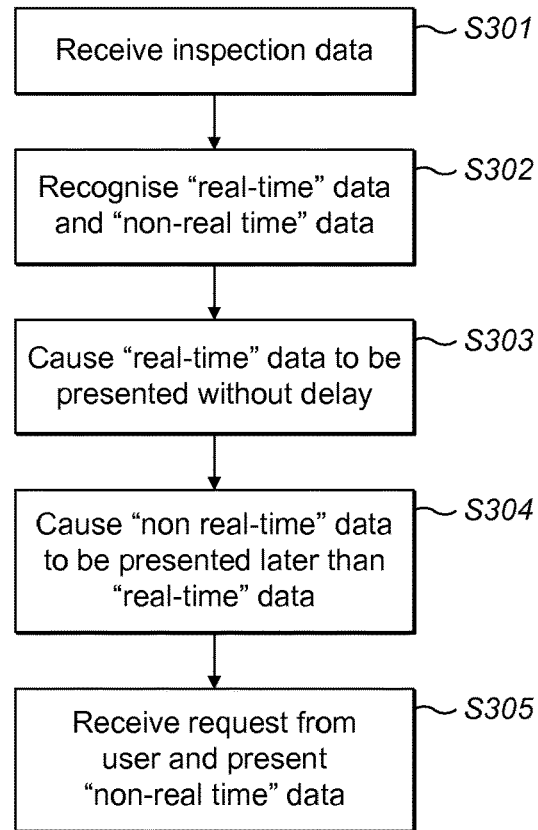
FIG. 3 shows an example of a method for operating a remote inspection apparatus.

The inspection apparatus at the remote site may also have a role to play in how inspection data is presented to the remote expert. The remote inspection apparatus shown in FIG. 1 includes a division unit 119. As shown in FIG. 3, when communication unit 116 receives inspection data from the inspection site, the division unit may recognise non-real time and/or real-time data in that inspection data (steps S301 and S302). It may then cause the real-time data to be presented to the expert at a first time (step S303). Suitably this presentation occurs directly upon the division unit recognising the real-time data so that it is presented without unnecessary delay. The non-real time data is preferably presented at a later time (step S304). The non-real time data may be buffered in the meantime (e.g. using memory 117 shown in FIG. 1). In some implementations the non-real time data may only be presented to the expert when the expert requests it (step S305).

As mentioned above, the non-real time data may be provided to facilitate more in depth analysis of the inspection data by the expert. One option is for the expert to manipulate the non-real time data to observe different aspects of the test object. The expert could, for example, adjust the time gates or change the filtering applied to the data to reveal different sections/aspects of the test object's condition. The expert is thus able to apply additional processing to the non-real time data, which may have originally been delivered to the remote inspection apparatus in a substantially unprocessed (raw) state. An advantage of the approach described above, in which data is split into real-time and non-real time data, is that it facilitates this kind of detailed analysis by the remote expert without hindering the real-time monitoring that makes meaningful interaction between the expert and the non-expert possible.

Returning to FIG. 1, it may be advantageous if the expert and non-expert can exchange information that will help the expert monitor the inspection process in addition to inspection data. For example, the inspection apparatus preferably includes a means for capturing video and sound so that the expert can: (i) watch the non-expert perform the inspection; and (ii) offer advice and issue instructions via a two-way voice link. The apparatus in FIG. 1 thus includes a video camera 104 and a microphone/loudspeaker arrangement 103. A corresponding microphone/loudspeaker arrangement 118 forms part of the remote apparatus. The arrangement shown in FIG. 1 thus envisages three different types of data being exchanged between the two sites: inspection data relating to the test object, audio data and video data. These different types of data might be transmitted together or separately, over an appropriate link. In one example, the microphone/loudspeaker arrangement might be provided by a mobile phone, with the video and inspection data being transmitted provided separately. In another example all three types of data might be transmitted using the WebRTC protocol, which supports the transfer of audio, video and data simultaneously.

The apparatus at the two sites are preferably connected via a peer-to-peer arrangement. Another option is for a server architecture to be used, but this type of arrangement is probably most suited to connecting "observers" into the inspection. So, for example, the remote expert's computer may be capable of providing multiple channels that observers can use to follow the inspection. In most implementations the observers are unlikely to exercise any control over the inspection process. The observers could be, for example, members of an insurance company that insures aeroplane 112, members of a local authority responsible for certifying experts, more junior inspectors who are training to become certified etc.

As well as interacting with the non-expert, e.g. via the two-way voice link, the apparatus preferably enables the expert to exert more direct control over the inspection process. Camera 104, for example, is preferably a PTZ (Pan-Tilt-Zoom) device configured to produce a live feed of video images under the control of the expert. This enables the expert to watch the non-expert carry out the inspection.

The expert may also be able to control settings on the inspection device. Examples of such settings might include pulse shapes or time gates. It may also be advantageous for the expert to have a degree of control over where the inspection device is placed on the test object. If the inspection device were under the control of a robot, such control would be straightforward, but robots are expensive and still have limited capabilities. The expert does have the ability to instruct the non-expert via the two-way communication link, but this does not precisely pinpoint a location on the test object where expert wishes the inspection device to be placed.

Figure 4:
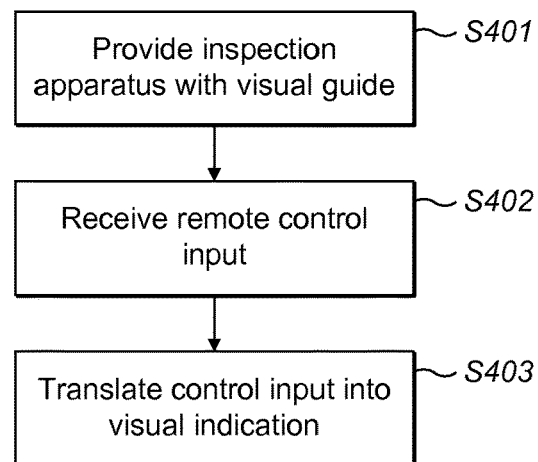
FIG. 4 shows an example of a method for providing a visual guide to a non-expert operating an inspection device.

An example of a method for addressing this issue is shown in FIG. 4. The method comprises providing the inspection apparatus with a visual guide (step S401). A control input is then received from the remote expert (step S402) and the visual guide is used to translate this control input into a visual indication for the non-expert about where to place the inspection device (step S403). Often this will take the form of a direction in which the expert wants the non-expert to move the inspection device.

Figure 5:
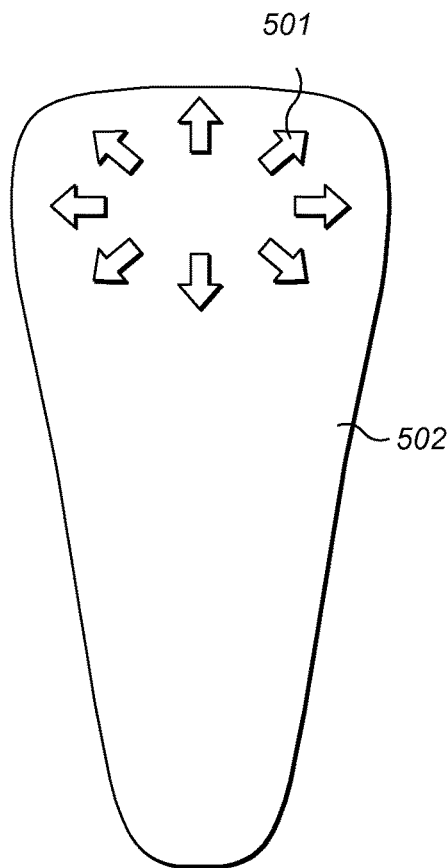
FIG. 5 shows an example of a visual guide on an inspection device.

There are a number of different options for implementing the visual guide. In one example, the visual guide includes some form of projection device. Suitably the projection device projects the visual indication for the non-expert onto the test object. An example of such a device is shown in FIG. 1. In this example the visual guide is a laser pointer 106 attached to camera 104. This is a convenient arrangement because: (i) the remote expert already has control of the direction in which the camera points; and (ii) since the camera and the laser are attached, they will point in the same direction, meaning that the expert should be able to see the projection of the laser onto the surface of the test object in the live video stream. Other arrangements are also possible, and the projection device could be controlled separately from the camera. Another option for the visual guide is shown in FIG. 5. In this example the inspection device is provided with a number of visual guides 501 on its back surface 502. In this example the visual guides take the form of a series of arrows that can be illuminated by the expert. The expert may use the arrow keys on his keyboard, for example, or a joystick, to illuminate the appropriate arrows on the back of the inspection device.

Figure 6:
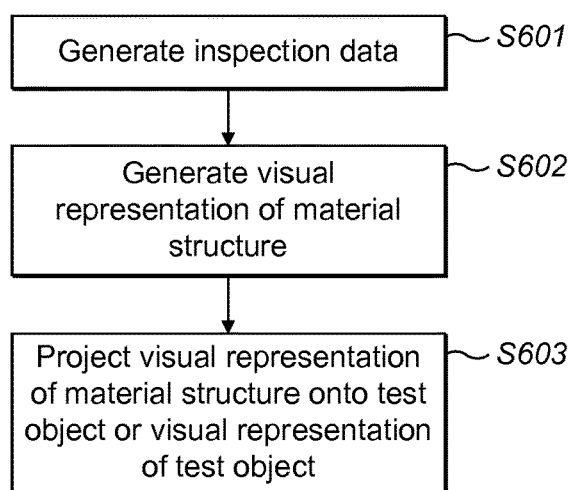
FIG. 6 shows an example of a method for enhancing situational awareness during an inspection.

An example of a method for enhancing the inspection procedure still further is shown in FIG. 6. In FIG. 6, an inspection device generates inspection data representative of the structure of a material comprised in a test object (step S601). Suitably the inspection device is capable of "looking" beneath the object's surface so that sub-surface flaws and damage in the material can be detected by the expert. This data is suitably used to generate a visual representation of the material structure (step S602). As mentioned above, a visual representation might be an A-scan, a B-scan, a C-scan or a 3D image. The visual representation is suitably generated by some form of image generator. The image generator might be comprised within the inspection device or it might form part of a separate computing device (not shown in FIG. 1). A projection device then projects the image of the material structure onto either the test object or a visual representation of that test object (step S603).

Figure 7:
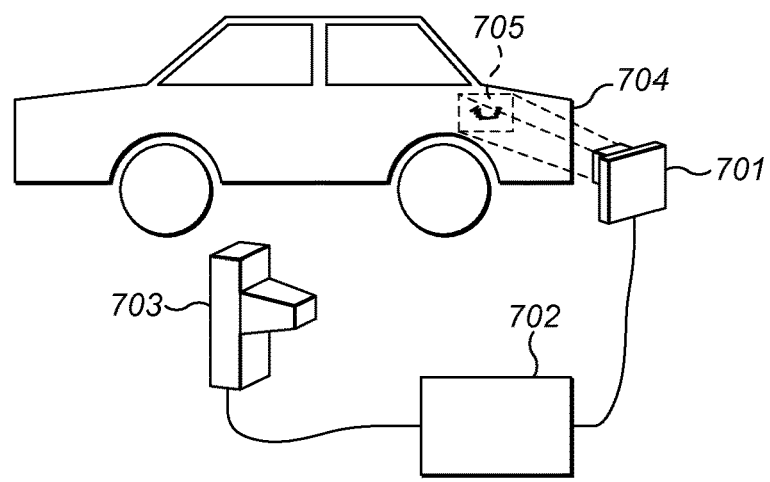
FIG. 7 shows an example of an apparatus for enhancing situational awareness during an inspection.

One example of such a projection device is shown in FIG. 7. In FIG. 7 the projection device is a video projector 701. It is connected to an image generator 702, which is in turn connected to an inspection device 703. The test object in this example is a car 704. The image generator is suitably configured to provide the video projector with one or more images generated from the inspection data. The video generator is then configured to project these onto the surface of the car 705. This provides enhanced situational awareness for both the expert and the non-expert.

Preferably the inspection images are projected onto the same part of the surface of the test object from which the inspection images were generated. The projection device is preferably moveable so that this can be achieved. It is preferred that the video projector be automatically moved into the correct position, as this is likely to be more accurate than relying on the non-expert projecting the inspection images onto the correct part of the test object's surface. This may be achieved by providing a positioning system as part of the inspection apparatus, which is capable of locating the inspection device within the positioning system and particularly its location in relation to different parts of the test object. The positioning system may comprise a series of sensors. These sensors may, for example, be configured to receive short-range, positioning transmissions from the inspection device. In other implementations the inspection device might have the ability to determine its own position, orientation and depth data.

Figure 8:
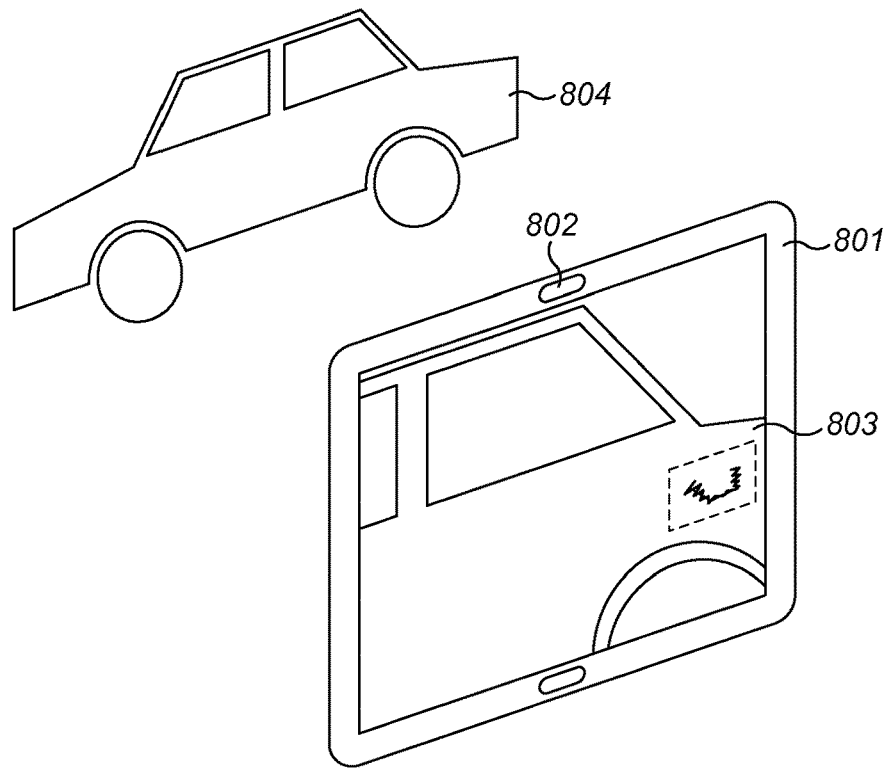
FIG. 8 shows an example of an apparatus for enhancing situational awareness during an inspection.

Another example of a projection device is shown in FIG. 8. In this example the projection device is a handheld computing device 801. Rather than projecting inspection images onto the surface of the test object itself, in this example the images are projected onto a visual representation of the test object. The handheld computing device may comprise a camera 802, so that the visual representation of the test object (car 804) is a video image 803 of that object. In another example the visual representation could be a 3D CAD model of the test object. The projection device could include a memory storing many of such CAD models, the appropriate one of which can be retrieved in dependence on a type or model number entered by the user. A system of this type may also use information gathered by a positioning system to position the inspection images on the appropriate section of the CAD model or video image. Another option is for the handheld device to incorporate one or more of position, orientation and depth sensors and/or a motion tracking camera so that it can determine its own position relative to the test object (which may be useful if the inspection images are being projected onto a video stream of the test object, for example). An advantage of this approach is that the projection device may also be used remotely if the appropriate data is communicated to it. For example, the projection device might be implemented on a PC of the remote expert.

Another way in which the inspection procedure may be improved is by incorporating the underlying structure of the test object into the inspection. For example, there may be some parts of a test object where damage is less significant than others. Impact damage in the material of an aeroplane may be less significant if it is in a part of the aeroplane that is significantly reinforced, for example. Conversely there may be some parts of an aeroplane that are inherently weaker due to the aeroplane's underlying structure. It may be beneficial to incorporate the test objects underlying structure into either of the projection examples described above. Another option is for areas of earlier damage and/or repair to be highlighted. For example, part of the internal structure of the test object may be projected onto the corresponding section of its surface, either alone or in combination with one or more inspection images. Similarly the internal structure of a test object may be projected onto a video stream or CAD model of the exterior of the test object. The same approach may be taken with projections highlighting areas of previous damage and/or repair. Again, these new images may be combined with the inspection images. The images of the object's underlying structure are preferably pre-generated and may be stored in the inspection apparatus under a type or model number corresponding to the particular test object. Records of previous damage and/or repair may be available from an inspection log relating to the particular object being inspected.

Figure 9:
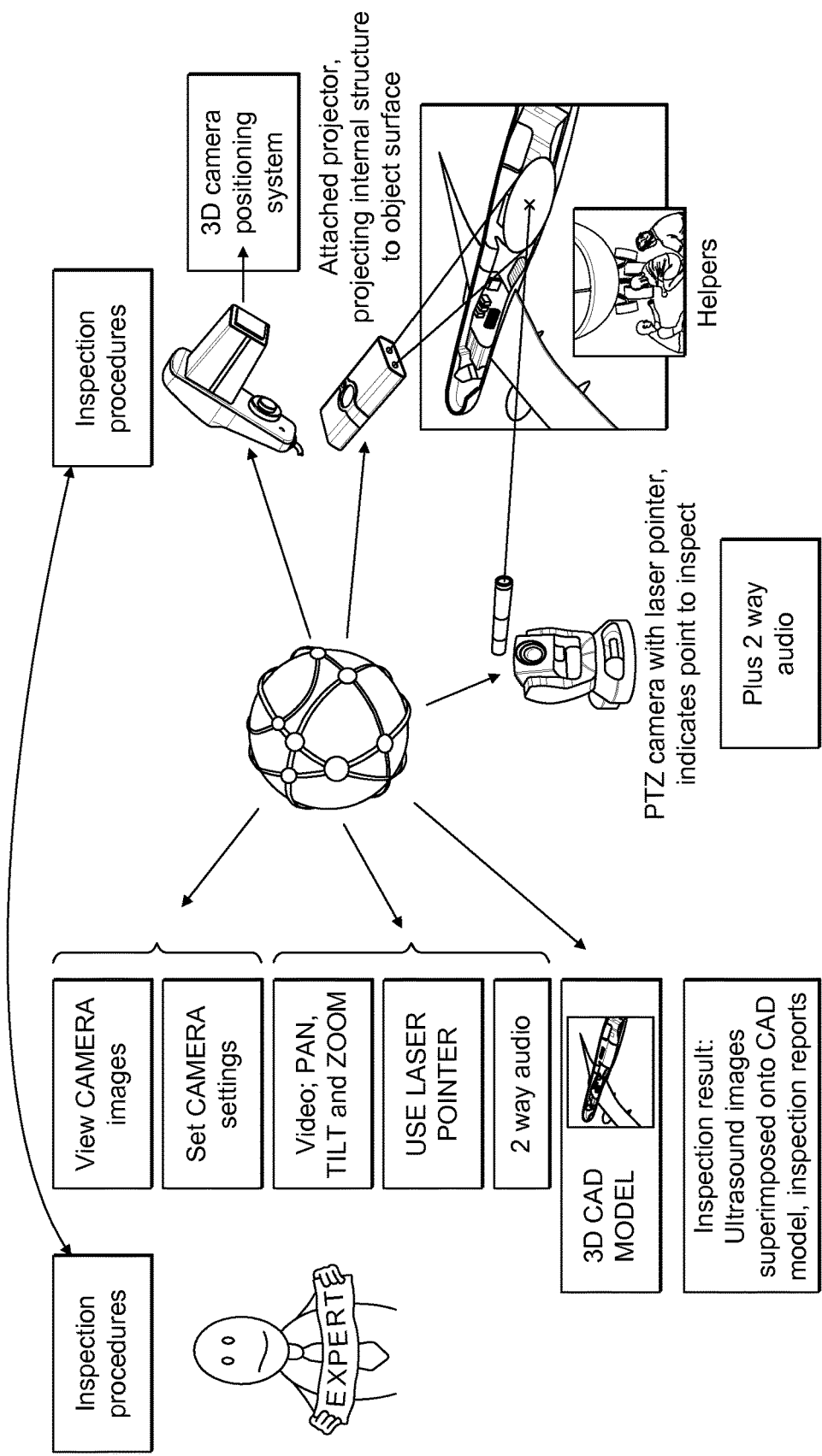
FIG. 9 shows an overview of an example inspection system.

An overview of an inspection system is shown in FIG. 9. The overview incorporates some of the projection examples described above. In FIG. 9 the system is illustrated for an implementation in which a remote expert is supervising a non-expert on-site. It should be understood, however, that the projection examples described above may equally be advantageously implemented in a straightforward inspection scenario in which the inspection is just performed on-site, with no remote supervision.

Figure 10:
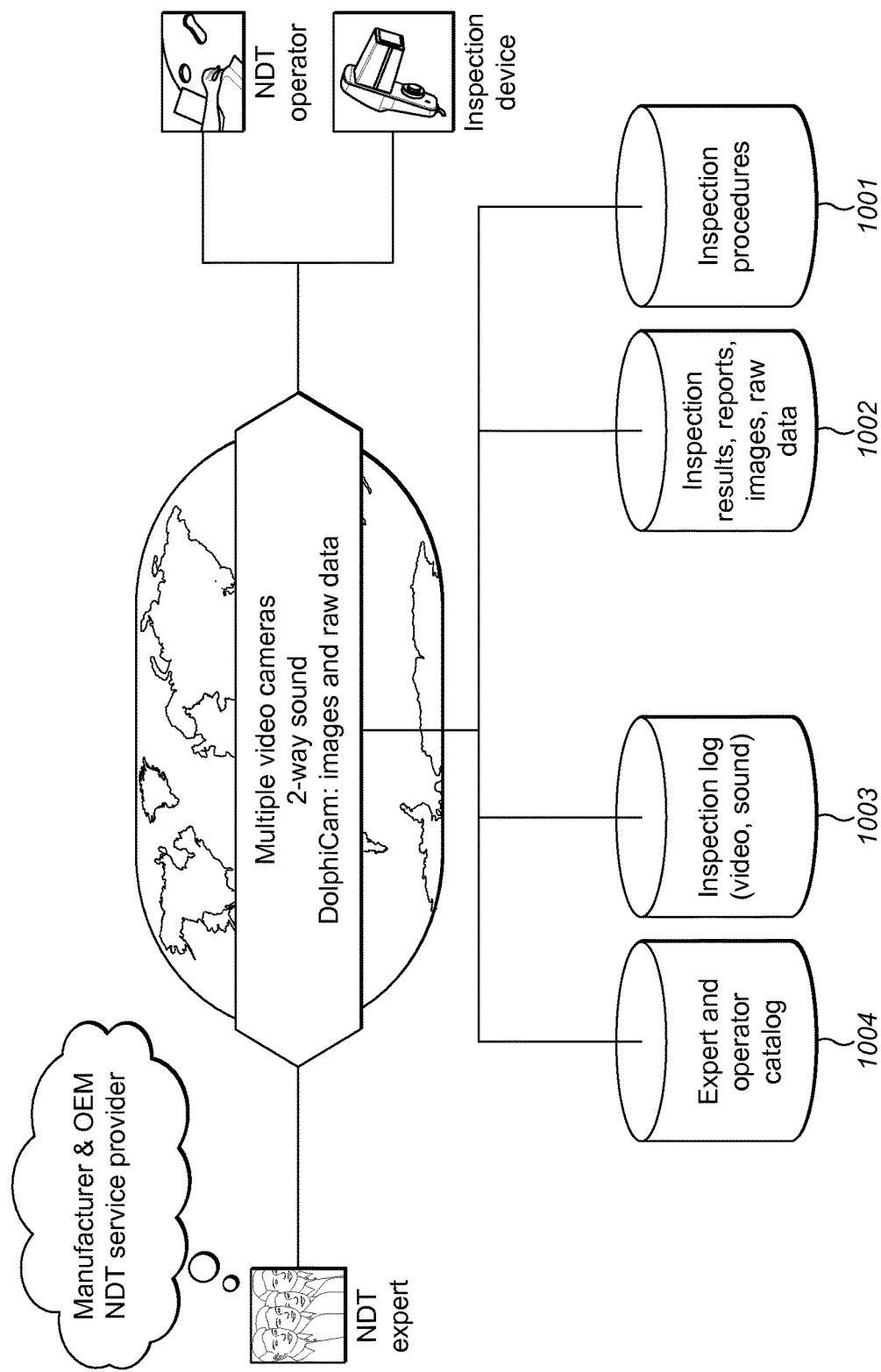
FIG. 10 shows an overview of an example inspection system.

A further overview of an inspection system is shown in FIG. 10. This illustration exemplifies the transfer of data between the inspection site and the remote site. It also illustrates the type of information that may be provided, generated and stored as part of a typical inspection process. An example of information that may be provided to the non-expert and/or the expert include the inspection procedures stored in memory 1001. Examples of information that may be generated as part of the inspection process include inspection results (e.g. any repair decisions that have been made), inspection reports, inspection images and raw data. These are shown as being stored in memory 1002 in FIG. 10. An inspection log may also be kept, and this may include audio and video images from the inspection (see memory 1003). An expert and operator catalogue 1004 may also form part of the inspection system. In FIG. 10, this catalogue is represented by memory 1004.

Figure 11:
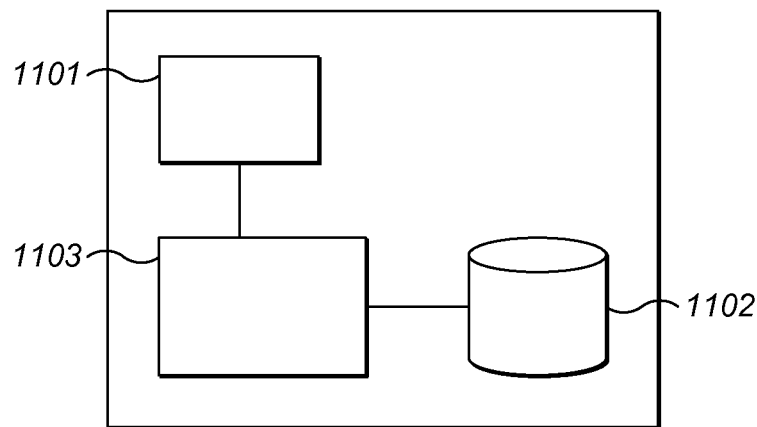
FIG. 11 shows an example of a directory.

The expert and operator catalogue shown in FIG. 10 may be implemented by a directory, such as that shown in FIG. 11. The role of the directory is to assist in connecting a non-expert inspector with a remotely-located expert. The directory comprises a communication unit 1101, a memory 1102 and a selection unit 1103. The memory is preferably configured to store a database of experts, along with their credentials. These credentials may include, for example, the experts' qualifications, a list of companies or authorities they are certified by, types of object they are qualified to inspect (e.g. aircraft or cars of specific types), earlier experience with relevant structures or test objects etc. The database may also store other relevant information, such as the experts' current availability, time zone, normal working hours etc. The database preferably also includes contact information for each expert.

Figure 12:
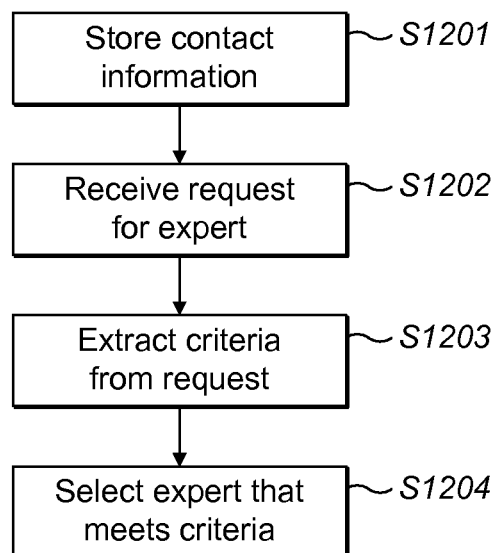
FIG. 12 shows an example of a method for obtaining expert contact information.

An example of a process for using the directory is shown in FIG. 12. In step S1201 contact information is stored for a plurality of experts. In step S1202 the communication unit receives a request for an expert. That request may have been sent by an inspection apparatus automatically, semi-automatically or in response to manual input. In step S1203, the selection unit extract, from the request, one or more criteria specifying the type of expert that is required. The selection unit is preferably configured to extract, from the request, criteria including one or more of: a location of the inspection apparatus, a type of test object being inspected by the inspection apparatus, an owner of the test object being inspected by the inspection apparatus and any legal requirement governing the inspection of the test object. The selection unit searches the memory for one or more experts that meet the criteria (step S1204). Suitably the selection unit prioritises some criteria over others. For example, the selection unit preferably only selects experts that have the necessary credentials for the inspection.

If an expert is currently unavailable, the selection unit may select him anyway if no other appropriately qualified experts are available. This is particularly applicable if the database indicates when an expert who is currently unavailable is likely to become free again, and that information indicates that the expert having the appropriate qualifications is likely to be available within a predetermined period of time. The selection unit may return contact details for the selected experts (step S1205) or, in a preferred embodiment, connect the requesting inspection apparatus to an appropriate expert automatically (step S1206).

In a preferred embodiment, the inspection apparatus may send the request for an expert without the user having to expressly request it. For example, if the user asks the inspection apparatus for a remote inspection procedure, that may trigger the inspection apparatus to automatically request the expert details, appropriate inspection procedures etc. from other parts of the system. The user may only be required to enter basic information such as the type or model number of the object to be tested. In one example, if the directory returns contact information for one or more experts to the inspection apparatus, the inspection apparatus may automatically select an expert and effect the connection. This may cause a connection request to be sent to the remote inspection apparatus, which the remote expert may choose to accept or not.

Figure 13:
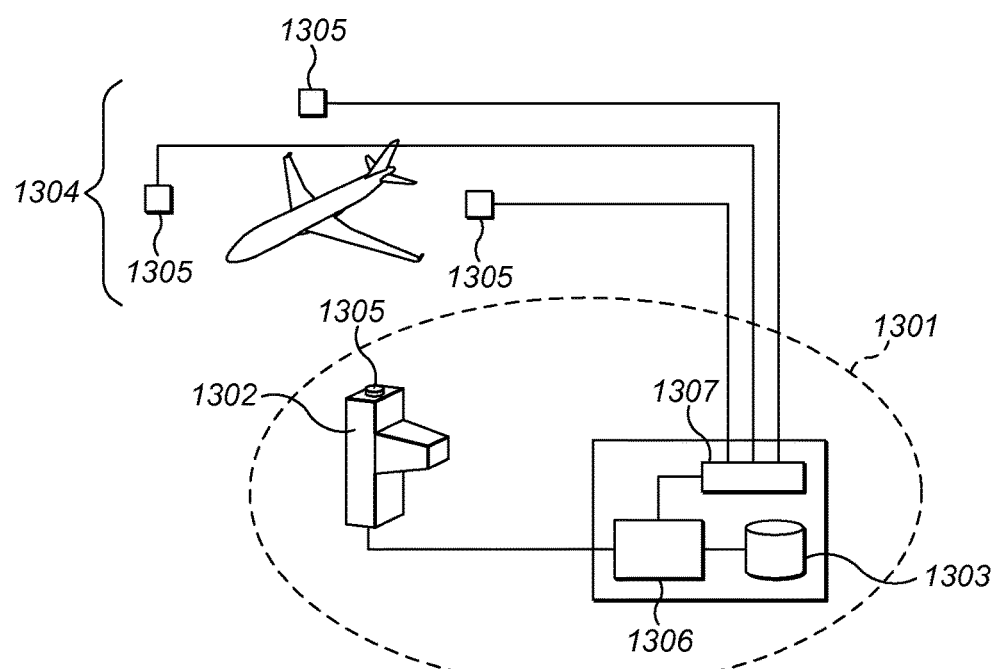
FIG. 13 shows an example of an inspection apparatus and a positioning system.

In one of the examples described above, the inspection apparatus may be implemented together with a positioning system. Providing an inspection apparatus with a positioning system can have other uses too, such as determining the position of the inspection device relative to the test object. An illustration of such a system is shown in FIG. 13. The inspection apparatus, shown generally at 1301, comprises inspection device 1302 and a database 1303. Database 1302 may be configured to store configuration data and/or test object records. Inspection apparatus 1301 also comprises a position determination unit 1307 that is configured to use information gathered by the positioning system to determine the position of inspection device 1302 relative to test object 1308. The inspection apparatus also comprises configuration unit 1306 that is configured to select appropriate configuration data from database 1303 and use it to configure inspection device 1302. The configuration unit may also use information from the database to generate configuration data where needed, optionally in conjunction with user input and/or previous inspection results.

The database 1303, configuration unit 1306 and position determination unit 1307 are shown in FIG. 13 as being comprised in a separate housing from the inspection device. They could, for example, be implemented by any suitable computing device, e.g. a PC, laptop, server etc. They might also be implemented together with other functional units, e.g. as part of communicator 106 shown in FIG. 1. The computing device is preferably configured to communicate with the inspection device (and the positioning system) via a wired or wireless connection. In other implementations these functional units could be implemented within inspection device 1302.

The inspection apparatus is shown in FIG. 13 together with positioning system 1304, which comprises sensors 1305. FIG. 13 shows an example of a time-of-flight positioning system in which the position of an object is determined by measuring the time that signals take to travel between a transmitted and a receiver. The transmitter may be comprised in inspection device 1302 and the receivers comprised in sensors 1305 or vice versa. Typically three time measurements are required to determine the three-dimensional position of an object. Another option is a spatial scan system, which uses beacons and sensors. The sensor may be in the inspection device and the beacon on the test object or elsewhere in the test environment or vice versa. This type of positioning system measures the angle between the beacon and the sensor to determine the position of the inspection device. In another example the inspection device may comprise an intertial sensing system such as one that measures rotation and/or position with a gyroscope and/or accelerometer. This type of system may not require any external sensors or references. An intertial sensing system will normally determine the inspection device's position relative to a known starting position, which could be a fixed point on a test object, such as the tail fin of an aeroplane. The positioning system may use one or more of optical signals, ultrasonic signals or radio waves. The positioning system might also be a hybrid system that uses a combination of two or more different positioning technologies.

The inspection apparatus may be configured to use information about the position of the inspection device relative to the test object to provide the inspection device with configuration data appropriate to the particular part of the test object that the inspection device assumes, from the inspection device's position, is about to be inspected. The configuration data is information that the inspection device can use to configure itself in the most appropriate way for that part of the test object. The aim is to automatically configure the inspection device to the part of the test object being tested, so that it generates the most accurate information possible about the condition of the test object and the material structure beneath its surface. Factors that may affect how the inspection device should be configured include the material of the part to be inspected, how far beneath the surface of the object the part to be inspected is, what level of detail is required (which may depend, for example, on whether that part of the test object has been previously repaired) etc. Configuration data might include, for example, one or more of: software routines, control settings, set-up information, operational parameters etc. More specifically, configuration data might include pulse shapes, time gate settings, pulse timings, pulse amplitudes etc.

The inspection apparatus device suitably has access to information detailing which configuration data is applicable to which particular part of a test object. In the arrangement of FIG. 13, for example, that information is stored in database 1303. In other arrangements the database may be stored elsewhere, and the inspection apparatus may access it remotely via a wired or wireless connection.

The information is preferably pre-generated, so that all the inspection apparatus has to do is access a record that gives the appropriate configuration data for a particular part. Alternatively, configuration data could be generated by the inspection apparatus during the inspection procedure. For example, the inspection apparatus may have access to a database of test objects, their respective parts and the relevant qualities of each and have the capability to select appropriate configuration data for each part accordingly. Relevant qualities may include information such as part type, part number, part structure, material etc. This type of information will generally be applicable across a particular class of test objects (e.g. a particular make and model of car or aeroplane). Other qualities in the database may be specific to a particular test object. For example, maintenance records for that particular test object, which may include details of previous damage or repairs.

The inspection apparatus may also be configured to select appropriate configuration data for the inspection device in dependence on user input (e.g. input from the inspector and/or a remote expert) and/or configuration data generated by the inspection device earlier in the inspection.

The inspection apparatus may be configured to supply the user with a list of possible parts to be inspected dependent on the position of the inspection device relative to the test object. The user may then select which of the parts he wants to inspect. This may be particularly applicable to complex test objects where more than one potential inspection target may lie below a particular position on the object's surface. Each potential inspection target may be associated with its own optimal configuration of the inspection device. The same mechanism may also be used if the accuracy with which the inspection apparatus is able to locate the inspection device means that its calculated position can be associated with several different parts of the test object.

Figure 14:
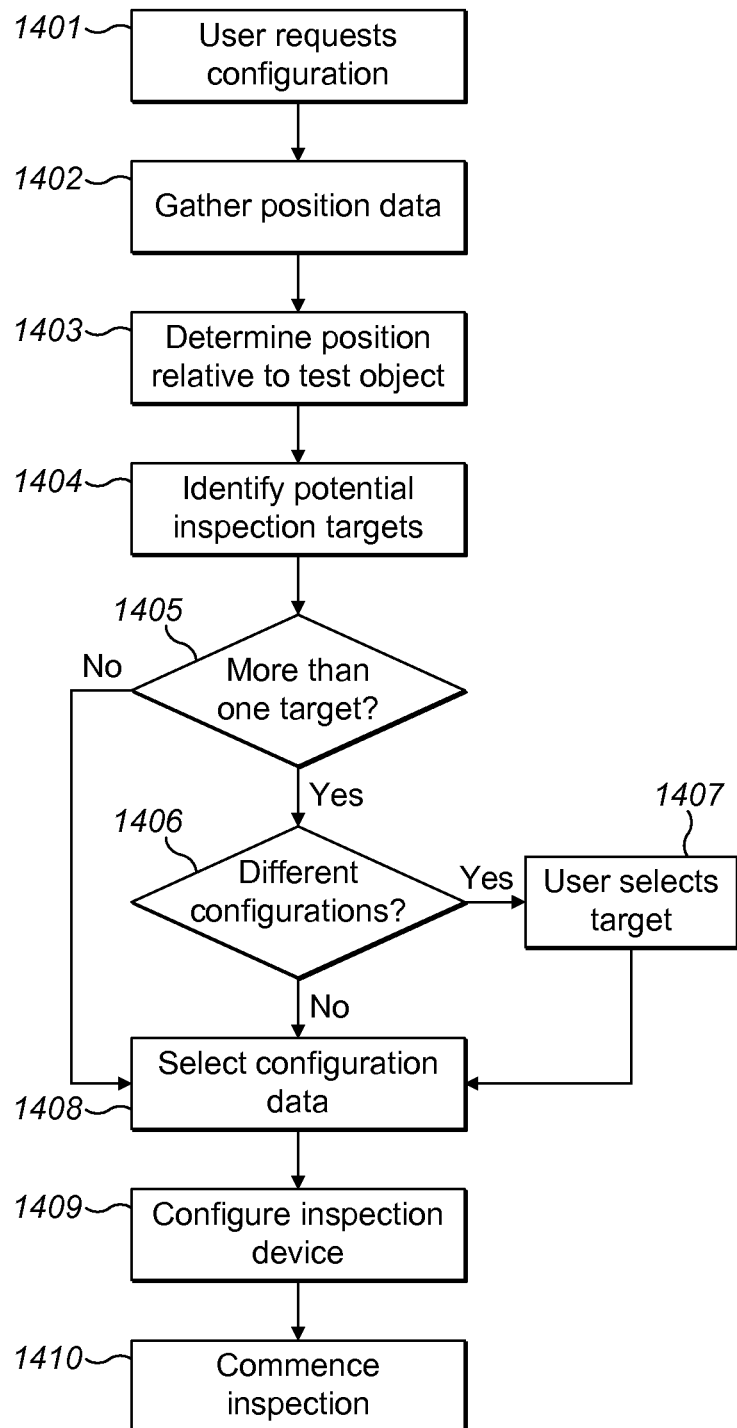
FIG. 14 shows an example of a method for configuring an inspection device.

An example of a method for configuring the inspection device in this way in shown in FIG. 14. The positioning process may optionally be triggered by user input (step 1401), e.g. by a user pressing a button on the inspection device when he is in position. The method comprises the positioning system then gathering position data associated with the inspection device (step 1402). This may include gathering data from various sensors positioned throughout the test environment or in the inspection device itself, in accordance with the particular positioning system that is being used. This data is then used to determine a position of the inspection device relative to the test object as a whole (step 1403). This step is suitably performed using the position data gathered in the preceding step. The position calculation itself may be performed by the positioning system, the inspection apparatus or may be divided between the two. The inspection apparatus preferably has the plans, dimensions, configurations etc of the test object available to it in its database so that the position of the inspection device relative to the object can be determined. The inspection device is therefore likely to be best placed to determine the position of the inspection device relative to the test object, although in some implementations it could pass the appropriate test object plans to the positioning system for it to perform the calculation. This enable a list of one or more possible inspection targets to be identified (step 1404). This list may, for example, take the form of a list of parts. If more than one possible targets is identified (step 1405) and they are associated with different configurations (step 1406), then user may select which of the available options he wants to inspect (step 1407). These steps are optional, as in some implementations only one inspection target will be identified. The appropriate configuration data is then selected and provided to the inspection device in order that in can configure itself in accordance with that configuration data (step 1405). The inspection device configures itself in accordance with the configuration data (step 1405). The inspection can then be commenced using the appropriately configured inspection device (step 1406).

The functions described above, such as of storing the database, calculating positions, identifying possible inspection targets and selecting appropriate configuration data etc, may be performed anywhere in the inspection apparatus, including in the inspection device itself. It is expected, however, that in most implementations one or more of these functions will be performed in a computing device located in a separate housing from the inspection device (as shown in FIG. 13).

In some implementations the test environment may be configured to assist the user in placing the test object in a predetermined location and with a predetermined orientation to assist with the position calculations. For example, this may just take the form of markings on the floor of an inspection bay to mark out how an aeroplane/car should be parked for the inspection.

One advantage of using information from a positioning system in the way described above is that it enables the inspection device to be automatically configured for the inspection. Thus the input of a remote expert is not necessarily required to configure the inspection device appropriately for an untrained inspector, although a remote expert may still participate in the inspection.

The structures shown in the figures herein are intended to correspond to a number of functional blocks in an apparatus. This is for illustrative purposes only. The figures are not intended to define a strict division between different parts of hardware on a chip or between different programs, procedures or functions in software. In some embodiments, some or all of the procedures described herein may be performed wholly or partly in hardware. In some implementations, the communication unit, division unit, image generator, projection device and selection unit may be implemented by a processor acting under software control. Any such software is preferably stored on a non-transient computer readable medium, such as a memory (RAM, cache, FLASH, ROM, hard disk etc.) or other storage means (USB stick, FLASH, ROM, CD, disk etc). Any of the functional units described herein, and the directory in particular, might be implemented as part of the cloud.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. An inspection apparatus for enabling a remotely-located expert to monitor an inspection by a non-expert, the apparatus comprising:
   an inspection device capable of being operated by the non-expert, which is configured to generate inspection data indicative of a sub-surface material structure of a test object; and
   a communication unit configured to:
      divide the inspection data into first data for transfer in substantially real time and second data comprising data indicative of a more detailed representation of the sub-surface material structure of the test object than the first data, whereby the second data enables a more in-depth analysis of the inspection than the first data, such that the first data is different than the second data;
      transfer the first data for being presented to the remotely-located expert at a first time, to facilitate substantially real-time monitoring of the inspection by the expert; and
      transfer the second data for being presented to the remotely-located expert at a second time, which is later than the first time, to facilitate non-real time monitoring of the inspection by the expert.

2. An inspection apparatus as claimed in claim 1, the inspection device being capable of generating data indicative of an interior structure of the object, without damaging said object.

3. An inspection apparatus as claimed in claim 1, the communication unit being configured to divide the inspection data such that the first data comprises fewer bytes that the second data.

4. An inspection apparatus as claimed in claim 1, the communication unit being configured to divide the inspection data such that the first data has been subject to more processing than the second data.

5. An inspection apparatus as claimed in claim 1, the communication unit being configured to divide the inspection data such that the second data is raw data.

6. An inspection apparatus as claimed in claim 1, the communication unit being configured to transfer the first data before the second data and/or at a higher data rate than the second data.

7. An inspection apparatus as claimed in claim 1, the communication unit being configured to transfer the first data over a higher capacity communication link than the second data.

8. An inspection apparatus as claimed in claim 1, the communication unit being configured to:
   receive a request from the remotely-located expert for the second data;
   retrieve the requested data from the buffer; and
   transfer the requested data to the remotely-located expert.

9. An inspection apparatus as claimed in claim 1, the inspection device being further configured to use a non-destructive testing technique from one or more of magnetic particle, liquid penetrant, eddy current testing, low coherence interferometry and ultrasound.

10. An inspection apparatus as claimed in claim 1, in which the communication unit is further configured to transfer the second data after the inspection device ceases generating new data.

11. An inspection apparatus as claimed in claim 1, the second data representing a more complex type of image than the first data.

12. A method for enabling a remotely-located expert to monitor an inspection by a non-expert, the method comprising:
   generating inspection data indicative of a sub-surface material structure of a test object;
   dividing the inspection data into first data for transfer in substantially real time and second data comprising data indicative of a more detailed representation of the sub-surface material structure of the test object than the first data, whereby the second data enables a more in-depth analysis of the inspection than the first data such that the first data is different than the second data;
   transferring the first data for being presented to the remotely-located expert at a first time, to facilitate substantially real-time monitoring of the inspection by the expert; and
   transferring the second data for being presented to the remotely-located expert at a second time, which is later than the first time, to facilitate non-real time monitoring of the inspection by the expert.

13. A method as claimed in claim 12, the method further comprising generating the inspection data using a non-destructive testing technique from one or more of magnetic particle, liquid penetrant, eddy current testing, low coherence interferometry and ultrasound.

14. A method as claimed in claim 12, in which dividing the inspection data into first and second data further comprises dividing the inspection data such that the first data comprises fewer bytes than the second data.

15. A method as claimed in claim 12, in which dividing the inspection data into first and second data further comprises dividing the inspection data such that the first data has been subject to more processing than the second data.

16. A method as claimed in claim 12, in which dividing the inspection data into first and second data further comprises dividing the inspection data such that the second data is raw data.

17. A method as claimed in claim 12, the method further comprising one or more of:
   transferring the first data at a higher data rate than the second data,
   transferring the first data over a higher capacity communication link than the second data, and
   transferring the second data after the inspection device ceases generating new data.

18. A method as claimed in claim 12, the method further comprising:
   receiving a request from the remotely-located expert for the second data;
   retrieving the requested data from a buffer; and
   transferring the requested data to the remotely-located expert.

* * * * *

UNITED STATES PATENT AND TRADEMARK OFFICE
CERTIFICATE OF CORRECTION

PATENT NO. : 10,503,157 B2
APPLICATION NO. : 14/855931
DATED : December 10, 2019
INVENTOR(S) : Jan Olav Endrerud and Eskil Skoglund Page 1 of 1

It is certified that error appears in the above-identified patent and that said Letters Patent is hereby corrected as shown below:

In the Claims

Column 16, Line 42, Claim 3, delete "bytes that" and insert -- bytes than --.

Signed and Sealed this
Fifth Day of May, 2020

Andrei Iancu
*Director of the United States Patent and Trademark Office*